United States Patent [19]

Stouffer

[11] Patent Number: 4,785,817
[45] Date of Patent: Nov. 22, 1988

[54] METHOD AND APPARATUS FOR ULTRASONIC GRADING OF MEAT

[75] Inventor: James R. Stouffer, Ithaca, N.Y.

[73] Assignee: Cornell Research Foundation, Inc., Ithaca, N.Y.

[21] Appl. No.: 917,562

[22] Filed: Oct. 10, 1986

[51] Int. Cl.[4] .............................................. A61B 10/00
[52] U.S. Cl. ................................. 128/660.07; 73/602
[58] Field of Search .............................. 128/660–663; 73/629, 602; 248/49, 58, 59, 61–62, 317, 323–324, 327, 333, 339–341

[56] References Cited

U.S. PATENT DOCUMENTS

| 1,823,149 | 9/1931 | Jordan | 248/340 |
| 2,007,820 | 7/1935 | Tucker | 248/61 |
| 2,252,820 | 8/1941 | Tallmon | 248/61 |
| 4,099,420 | 7/1978 | Stouffer et al. | 73/629 |

OTHER PUBLICATIONS

SAC Science Accessories Corporation, "Grafbar* Model GP-7 Sonic Digitizer", Technical Bulletin, GP-7-3-82.
Stouffer, J. R. et al., "A Review of Ultrasonic Applications in Animal Science", *Journal of Clinical Ultrasound*, pp. 124–128, 1977.
Kester et al., "Beef Industry Shoots for Electronic Grading Prototype Within Five Years", *Beef*, pp. 6–10, Aug. 1985.
Cross, R., "Instrument Grading", *Meat Industry*, pp. 54–58, Oct. 1981.
Crawford, L., "Crosscurrents", *Science* 86, pp. 64–65, Mar. 1986.

*Primary Examiner*—Francis J. Jaworski
*Attorney, Agent, or Firm*—Jones, Tullar & Cooper

[57] ABSTRACT

An improved transducer positioning device for use in evaluating fat thickness and muscle area at a selected rib area of a hog carcass, and for evaluating fat thickness and muscle score, of the ham portion of the carcass, is disclosed. A system for displaying ultrasonic images on a monitor and for measuring and analyzing the imaged areas for use in grading the quality of the carcass is also described. The transducer positioning device consists of a transducer support arm adapted to hold a rib area transducer in the proper position against a carcass for measurement of fat thickness at a selected rib area. The support arm includes a connector hook for attaching it to the tail of the carcass so that the transducer is accurately positioned over the rib area to be measured. In addition, a ham transducer is mounted in a collar attachment for connection to the rear leg of a hog carcass to provide an accurate measurement of fat thickness and muscling of the ham. The transducers produce real time scanned ultrasonic images which are displayed on a monitor for immediate evaluation of, and grading of, the carcass. The images are also recorded for later display on remote monitoring devices for more detailed analysis and grading by suitable pattern recognition techniques.

22 Claims, 4 Drawing Sheets

METHOD AND APPARATUS FOR ULTRASONIC GRADING OF MEAT

BACKGROUND OF THE INVENTION

The use of ultrasonic techniques in the evaluation of the meat yield and quality of livestock has gradually been developing over the past few years, and it is now well established that such techniques provide a feasible way to grade the qaulity of animal carcasses. U.S. Pat. No. 4,099,420 to Stouffer, assigned to the Asssignee of the present application, discloses one such technique for obtaining measurements needed for carcass measurement and inspection, but it has been found that the device disclosed therein not only is too complex, but does not provide, in an accurate, reliable, and consistent manner, the information needed for rapid evaluation and grading of carcasses.

After a meat animal such as a hog is slaughtered, it may be graded for quality by a grader who evaluates each carcass. At the present time, this grading is done by a visual inspection. Because the grade assigned to a carcass determines the price at which it can be sold, the grading has a significant economic impact. However, as is well known in the industry, this is a highly subjective evaluation of the carcass, and since small variations in grading can have an extremely large economic impact on a large producer, there is a strong economic pressure to make the process more objective, so that grading will more accurately reflect the true value of the carcass.

The ultrasonic techniques exemplified by the aforementioned U.S. Pat. No. 4,099,420 have helped to overcome the problem of subjective judging, for such devices have shown that through the use of ultrasonic transducers, it is possible to obtain an accurate reading of the fat content and muscling of not only carcasses, but live animals as well. However, the mere existence of ultrasonic techniques has not solved all of the problems that have been encountered in the grading of meat. For example, in order to get consistent and comparable results, it is necessary to measure in the same location on the carcass each time and to compensate for the fact that the multiple layers of fat in a hog carcass produce multiple readings in an ultrasonic transducer. Furthermore, since many available transducers are not able to scan a complete cross-section of an area of interest, time consuming multiple readings and interpretations have been required, and since it is necessary, on a commercial scale, to be able to grade hog carcasses at a high rate of speed, for example, 300–1000 carcasses per hour, speed and ease of operation of any ultrasonic device becomes essential. It has been found that devices such as that illustrated in U.S. Pat. No. 4,099,420 are too complex to permit the rapid use required for commercial evaluation of hog carcasses, for such devices have required the use of coupling fluids, spring-loaded transducers, multiple readings, and the like to accommodate to different shapes and sizes of carcasses as they pass by a grading station. Such complexities slow down the evaluation process and do not provide the economies that are necessary to make the conversion to ultrasonic grading techniques economically feasible at the present time. What is required, then, is a transducer device that will provide rapid, reliable information concerning a carcass, and will provide information that can be used quickly and easily for a more accurate evaluation and grading of the carcass than is possible through visual inspection. Absent an improved rate and accuracy of reading, a mechanical device for evaluation will not find acceptance in the industry.

SUMMARY OF THE INVENTION

It is, therefore, an object of the present invention to provide a method and apparatus for rapidly and accurately measuring fat content and meatiness for use in grading a carcass.

A further object of the invention to provide a method and apparatus for attaching ultrasonic transducers to carcasses in such a way that the transducers will be properly positioned for measuring, by ultrasonic waves, the fat content and meatiness of the carcass and for providing that information in a form which can be used to grade the carcass in a rapid and reliable manner.

It is a further object of the present invention to provide ultrasonic transducer mounting devices for securing transducers at selected locations on a carcass, the mounting devices serving to mount the transducers at the same location on each carcass for consistency in measurements.

It is a further object of the present invention to provide mounting apparatus for transducers wherein the mounting apparatus is quickly and easily secured to a carcass for positioning the transducers at desired locations thereon for accurate and reliable measurement of the fat content and meatiness of the carcass.

A still further object of the present invention is to provide apparatus for easily and reliably positioning transducers on a hog carcass in a preselected location so that measurements of successive carcasses will be made in the same location rapidly and without error.

It is a still further object of the present invention to provide a method and apparatus for evaluating the ultrasonic images produced by rib area and ham area transducers on a hog carcass in order to produce an automatic evaluation of the fat thickness and meat area measured by the transducers and to automatically grade the carcass.

Briefly, the present invention relates to an ultrasonic system incorporating transducer positioning devices for use in evaluating fat thickness and muscle area at the last rib area and, optionally, at the tenth rib area, of a hog carcass, and for evaluating fat thickness and muscling in the ham portion of a hog carcass. The positioning devices include a support unit adapted to hold a first rib area transducer in the proper position against a hog carcass for measurement of fat thickness and meatiness at the last rib, and a collar unit for holding a ham area transducer in position for measuring the fat content, meat score, and profile of the meat in the ham area of a hog carcass. In addition, or alternatively, the support unit may carry a second rib area transducer positioned to measure fat thickness and meatiness at the tenth rib of the carcass.

The rib area support unit includes a transducer support arm of predetermined length and having at one end a connector for attaching it to the tail of the carcass. The transducer support arm is selected to be of the correct length so that when so attached, the rib area transducers will be accurately positioned over the rib areas to be measured. It has been found that a fixed length arm can be provided, since hog carcasses will essentially all have their last rib area and their tenth rib area located a fixed distances from the tail. The support arm thus gives a consistent and reliable reading of the thickness of the back fat at the areas on the carcass which have been found to provide an accurate indication of the fat and lean content throughout the carcass and thus permits an accurate judgement to be made of the grade of the carcass as a whole.

Although only a single rib area transducer at the last rib is needed for good accuracy in grading the carcass, it has been found that improvded accuracy in grading can be attained by adding an additional rib area transducer in the region of the tenth rib of a hog carcass.

To further improve the accuracy of the grading, another measurement may be made in the ham area of a hog carcass by providing a ham area transducer, which can be the same transducer as that used in making the rib area measurements, which is mounted on the carcass by a second transducer support device, or collar attachment. The collar attachment is formed at one end with a C-shaped arm which partially encircles the leg of a hog carcass. The opposite end of the collar carries a transducer clamp which secures the ham area transducer to the collar in the proper location below the C-shaped arm to insure that the ham area transducer hangs down from the collar and is properly positioned for measurement of the meatiness of the ham, when the carcass is suspended from an overhead hook.

Both the rib area and the ham area transducers provide scanning and read-out signals which reflect the fat content of the carcass adjacent the location of the transducer. As is known, the transducers produce ultrasonic waves which are directed into the carcass, with portions of the waves being reflected at the interfaces between fat and muscle, to thereby produce output signals representative of the fat content and its location within the carcass. The display of this information permits an immediate visual evaluation of the grade of the carcass, and since the transducers produce an accurate output at the same location on each carcass, consistent evaluations can be made.

The display can be visually reviewed so that the grader can supply a grade to the meat based on the ultrasonic readout without inspection of the carcass itself. In addition, the present invention provides an apparatus and method for automatic interpretation of the transducer readout for an even more objective evaluation of the carcass. Accordingly, the displayed information, which is in the form of a rib area fat and meat distribution image, or in the form of a ham area fat and meat distribution image, can be evaluated through pattern recognition techniques which will provide a printout or display of calculations based on the rib area and ham area images. These calculations can, for example, provide a measure of meat content or fat thickness, to permit a more accurate and objective measure of the yield of the carcass. In accordance with one aspect of the present invention, this is accomplished by displaying an image, representing, for example, the rib area transducer output, and by tracing the image, as by means of a digitizer, to provide data concerning the meat area and/or the thickness of the fat layer. The digitizer converts the traced image into a series of mathematical coordinates which are supplied to a computer for calculation of the area and thickness represented by the display in accordance with known calculation techniques. Although the present invention is described in terms of the use of a digitizer for such measurements, it will be apparent that other pattern recognition techniques may be used to determine the areas of the ultrasonic images obtained from the carcass.

BRIEF DESCRIPTION OF THE DRAWINGS

The foregoing and additional objects, features and advantages of the present invention will become apparent to those of skill in the art from a consideration of the following detailed description of preferred embodiments, taken in conjunction with the accompanying drawings, in which.

DESCRIPTION OF PREFERRED EMBODIMENTS

Figures 1, 2:
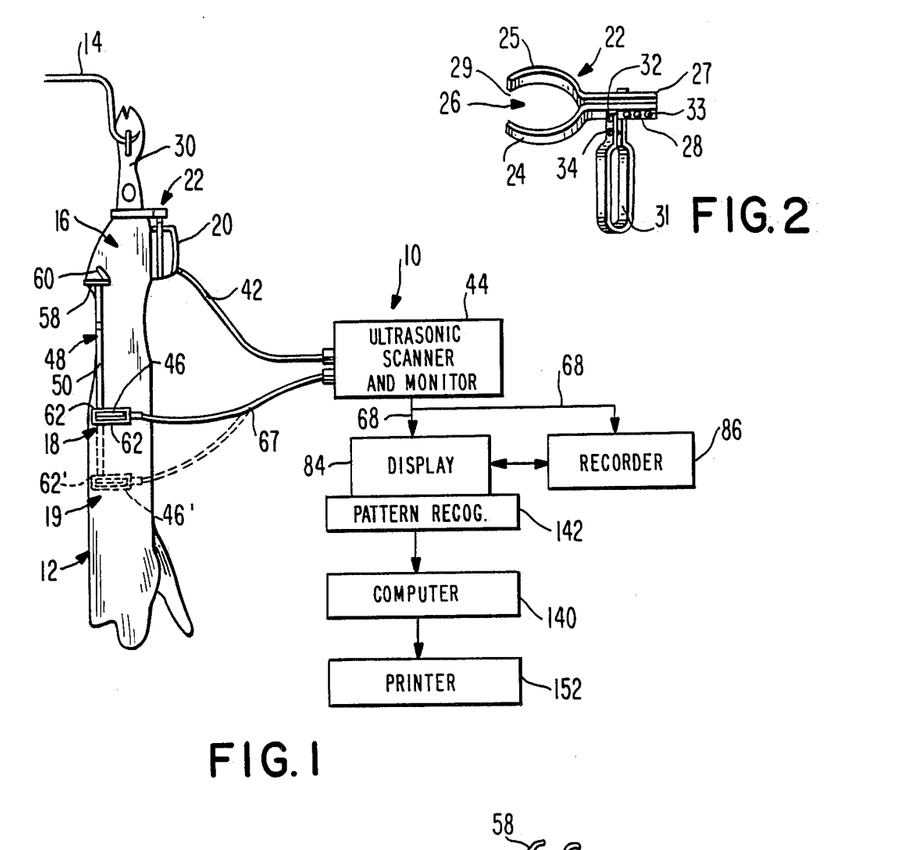
FIG. 1 is a diagrammatic illustration of the system of the present invention employed in the evaluation of a hog carcass.
FIG. 2 is an enlarged, perspective view of the ham portion transducer collar used in the system of FIG. 1.

Turning now to a more detailed consideration of the present invention, there is illustrated in FIG. 1 a grading system 10 in accordance with the present invention for evaluation and grading of carcasses such as the hog carcass illustrated diagrammatically at 12. The illustrated carcass 12 is split, as in general commercial practice, and is suspended vertically from a hook 14 for grading and for further processing. Although a split carcass is shown, it will be understood that the present invention is equally applicable to use with an intact carcass. In grading the carcass 12, it is necessary to inspect it for a variety of factors which are weighted and combined to determine the grade. Thus, it is necessary to determine fat thickness on the carcass, the amount of the muscling, as well as the hot carcass weight. Thse factors are then used to determine the grade which will be assigned to the carcass and which then will determine its value.

Because of the subjective nature of grading in the past, only five grades (1-5) were used, thus providing a very general grading system. Since only portions of a hog need to be measured in order to grade, the relevant measurements are made in the ham area 16, which consists of the upper part of the rear leg of the hog, and along the backbone of the hog, in the area of the last rib illustrated at 18 in the preferred form of the invention. In the past, it was thought that accurate grading required measurement of the back fat in three areas along the backbone in order to obtain an accurate grading of the carcass, and this led to complex measuring devices. However, it has now been found that an accurate measurement for purposes of grading can be obtained by a single measurement for back fat in the region of the last rib 18 of the hog. As an option, however, a second measurement of back fat may be made in the region of the tenth rib, at area 19, in order to improve the accuracy of the grading. Accordingly, the present invention provides a measuring device adapted to determine the back fat and muscle area at one or two selected locations only, thereby simplifying the measurements as well as the apparatus required, and increasing not only the ease of use, but the reliability of the measurements.

Figure 3:
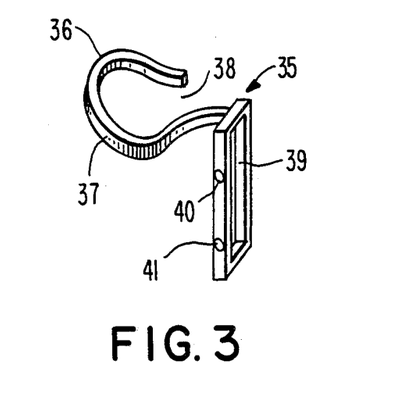
FIG. 3 is a perspective view of an alternate form of the collar of FIG. 2.

As shown in FIGS. 1, 2 and 3, measurements are made in the ham region of the carcass 12 by means of a ham area transducer 20 which is positioned vertically on the carcass 12 by means of a collar attachment 22. This attachment includes, in one form of the invention, a pair of clamping arms 24 and 24 which are curved at one end to form a generally C-shaped collar 26, and are parallel to each other at the other end to provide clamp support arms 27 and 28. The collar 26 has an opening 29 adapted to receive the leg 30 of a carcass, so that the collar will slide downwardly along the leg to the ham region 16 where the thickness of the leg becomes great enough to engage the collar and prevent it from sliding any further. The collar diameter is selected so as to stop the motion of the collar in such a location that the transducer 20 is properly positioned over the ham region to provide the desired measurement. The transducer 20 is secured to collar 26 by means of a depending clamp 31 which receives and secures transducer 20. Clamp 31 is secured to the clamp arms 27 and 28 by means of a suitable fastener 32 such as a nut and bolt, rivet, or the like, passing through corresponding apertures 33 formed in the arms. An adjusting screw 34 may be provided to tighten the clamp 31 around the transducer 20 to secure it in place for easy handling.

An alternate form of the collar attachment is illustrated at 35 in FIG. 3. In this embodiment, the attachment is formed with a C-shaped collar 36 which is formed by a curved arm 37. The collar has an opening 38 which receives the leg 32 of a carcass to allow the collar to slide down to the ham area 16, as described with respect to collar attachment 22. The curved arm 37 carries at one end a depending clamp 39 which is fixed to the arm, and which is shaped to receive the transducer 20. A pair of threaded fasteners 40 and 41 extend through the side of clamp 39 to secure the transducer in place.

Transducer 20 is a conventional ultrasonic scanning head having a linear array of transducer elements which sequentially send ultrasonic bursts and receive returned echoes in known fashion. The transducer head 20 is connected by way of cable 42 to a conventional ultrasonic scanner 44 such as an Aloka 210DX Linear Array Ultrasound System produced by Aloka, Inc., and distributed by Corometrics Medical Systems. This device produces ultrasonic waves at 3 or 5 MHz, detects reflected waves, and incorporates a small monitor screen for display of the return image detected by transducer head 20.

Figure 4:
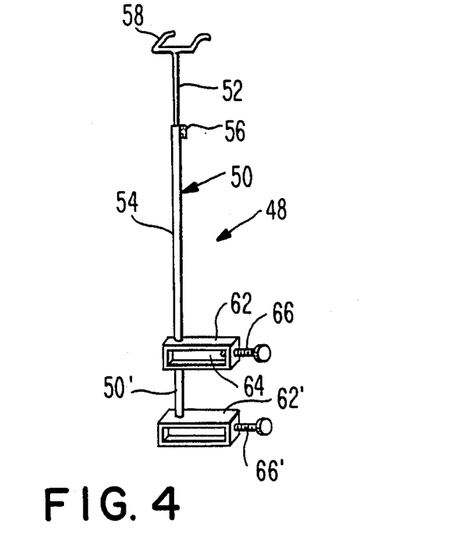
FIG. 4 is a perspective view of a rib area transducer support unit.

Measurement of the last rib area 18 of the hog carcass is obtained from a seond transducer head 46, which may be identical to transducer 20, or may be a slightly smaller version of such a transducer, and which is secured in a horizontal position by means of a rib area transducer support unit generally indicated at 48 in FIG. 4. The support unit 48 includes a support arm 50 which may be solid, or which may consist of upper and lower telescoping sections 52 and 54 secured at a desired length by a suitable fastener 56. Arm 50 includes at its upper end a connector hook 58 which is generally U-shaped and is adapted to fit over the tail 60 of the hog carcass. It has been found that the distance between the tail and the last rib area 18 of hog carcasses is generally the same, normally about 16 inches, so it is usually not necessary to adjust the support arm 50, although it may on occasion be desirable to do so for greater accuracy. The length of arm 50 is selected to position the transducer 46 over the last rib area of the hog when the connector loop 58 is secured over the hog's tail 60.

The transducer 46 is secured to the support arm 50 by means of a generally rectangular support bracket 62 secured to the bottom end of arm 50. The bracket has a generally rectangular interior opening 64 which is sized to receive a standard transducer head, and preferably includes a threaded screw 66 or similar fastener for securing the transducer head in the support unit 48.

In order to obtain a more accurate measurement of carcass back fat, it may be desirable to provide a second support bracket 62', secured to the bottom end of a support arm extension 50' secured to the bottom of bracket 62. The support arm extension 50' is sufficiently long to locate bracket 62' about 23 inches from the connector hook 58 so that bracket 62' will support an additional rib area transducer over the region of the tenth rib of the carcass, located at area 19 (FIG. 1). The bracket 62' includes an opening 64' and a threaded fastener 66' for receiving and securing an additional transducer 46', shown in phantom in FIG. 1.

The transducer head 46, and head 46', if used, both include a linear array of transducer elements, in conventional manner, which are held by the transducer support unit 48 in a generally horizontal position, with transducer 46 over the last rib area of the hog carcass, and transducer 46' over the tenth rib area. The transducers are connected by way of cable 67 to the ultrasonic scanner and monitor 44, which is capable of selecting between transducer 20, transducer 46 and transducer 46', if used, for taking measurements and providing the required image displays.

In use, the transducer 20 is positioned on the rear leg of the hog by hanging collar attachment 22 or 35 on the leg 30 of the carcass so that the transducer hangs vertically along, and in close contact with, the outer surface of the ham portion 16 of the carcass 12. The surface of the carcass normally is wet from being washed with water prior to the grading process, and the moisture on the surface provides sufficient contact between the transducer and the carcass to permit transmission of ultrasonic waves from the transducer into the ham area.

At the same time, the support unit 48 is secured to the tail of the hog carcass so as to locate the rib area transducer 46 over the region of the last rib, and to locate the rib area transducer 46', if used, over the region of the tenth rib. Both transducer 46 and transducer 46' are supported to extend horizontally, from the region of the backbone outwardly over the ribs of the carcass. Although the splitting of a carcass allows a visual inspection of the back fat along the backbone, it has been found that a more accurate measurement is obtained in the area to one side or the other of the backbone, which is where the transducers 46 and 46' are placed. Accordingly, it is not necessary to split the carcass in order to obtain the desired measurement, by using the apparatus of the present invention. The rib area transducers 46 and 46' are placed in intimate contact with the surface of the carcass, using the moisture on its surface to insure good transmission of the ultrasonic waves.

The images received by the several transducers, produced by the reflection of ultrasonic waves from discontinuities within the carcass, are fed to the scanner 44 by way of cables 42 and 67 for display on its monitor. The images may also be transmitted by way of cable 68 to suitable remote equipment such as a display unit or a video cassette recorder to be described. The monitors or the remote display unit may be used by a grader to evaluate and determine the grade to be assigned to the carcass. The monitor is also available to the equipment operator to make sure that a proper image is being obtained.

Figure 5:
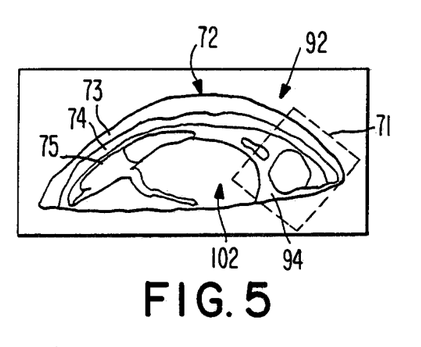
FIG. 5 is a diagrammatic illustration of the last rib area of a carcass from which the image of FIG. 6 was obtained.
Figure 6:
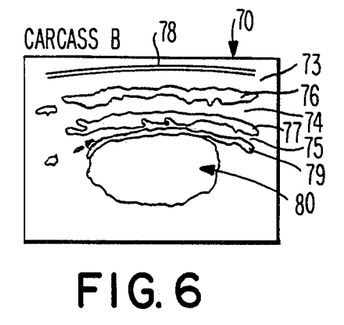
FIG. 6 is a diagrammatic illustration of a transducer image produced from the rib eye area of the last rib of a first hog carcass, illustrated in FIG. 5.

FIG. 5 is a diagrammatic illustration of the carcass cross-section, while FIG. 6 illustrates a typical image 70 derived from a rib area of the carcass by a transducer head such as that illustrated at 46 or 46'. The image is derived from the rib eye, or loin eye, portion 71 of the carcass section 72 illustrated in FIG. 5. The image 70 shows three layers of fat at 73, 74 and 75, as is conventional in hog carcasses, separated by connecting tissue 76 and 77, and covered by a skin layer 78. Another layer of connecting tissue 79 separates the fat layer 75 from the rib eye meaty portion, indicated at 80. In the particular carcass illustrated in FIG. 5, relatively heavy layers of fat are shown. This image, which was taken from a test of the herein disclosed equipment, was displayed on the monitor of scanner 44 during the operation of transducer 46 to allow the operator of the equipment to make sure that a good image was being obtained. This same scanner image may be viewed by a grader at the monitor or at a remote display 84 connected to the monitor by cable 68, for "real time" grading purposes, or it may be transferred via cable 68 to recorder 86 for later display and grading. It will be understood that when the image is to be recorded for later evaluation, it is necessary to incorporate in the recording suitable data to identify the carcass from which the information was obtained so that the grade can be assigned to the proper carcass.

FIG. 5 shows the location of a backbone 94 and the three heavy layers of fat at 73, 74 and 75. Beneath the fat layers is the rib eye area 80.

Figure 7:
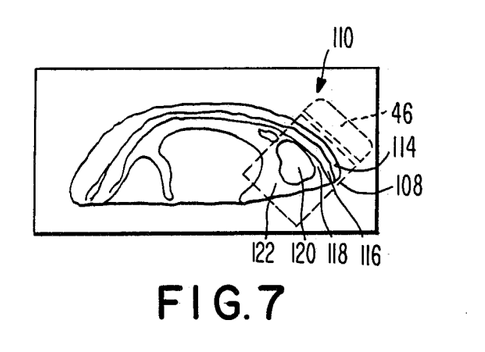
FIG. 7 is a diagrammatic illustration of the last rib area of the carcass from which the image of FIG. 8 was obtained.
Figure 8:
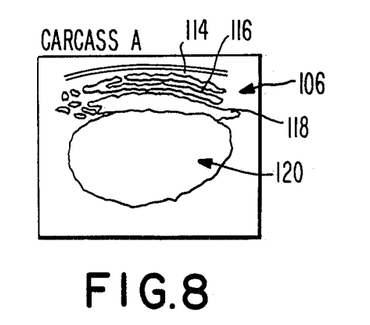
FIG. 8 is a diagrammatic illustration of a transducer image from the last rib eye area of a second hog carcass, illustrated in FIG. 7.

FIGS. 7 and 8 ilustrate diagrammatically a rib eye ultrasonic image 106 taken from the region 108 of the cross-section of a second carcass 110, it being understood that the transducer 46 is positioned on the carcass as illustrated at 46, carcass 110 having a significantly lower amount of fat than was present in the carcass illustrated in FIGS. 5 and 6. As shown, the fat layers 114, 116 and 118 are significantly thinner than those of the hog carcass illustrated in FIGS. 5 and 6, while the meaty area 120 is greater. The rib and backbone 122 is shown in FIG. 7, but does not appear clearly in the diagrammatic image of FIG. 8. FIGS. 5-8 illustrate that the transducer 46 is capable of producing images of sufficient clarity to permit an accurate determination of the back fat and meatiness in the rib area of the carcass for accurate and reliable grading.

Figure 9:
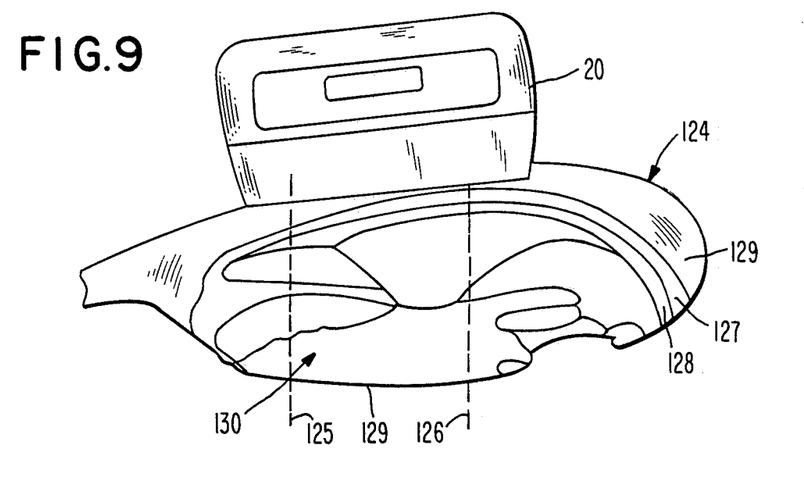
FIG. 9 is a diagrammatic illustration of the ham area of a hog carcass, to be measured by a ham area transducer.
Figure 10:
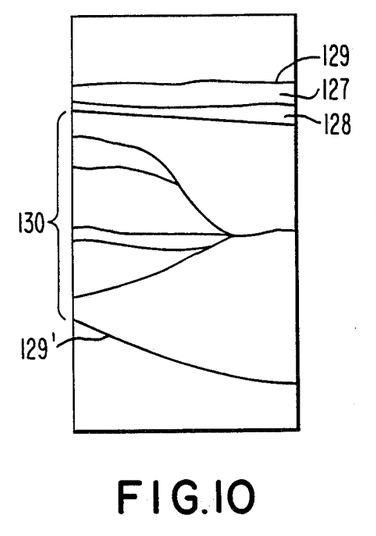
FIG. 10 is a diagrammatic illustration of an ultrasonic transducer image obtained from the ham area of FIG. 9.
Figure 11:
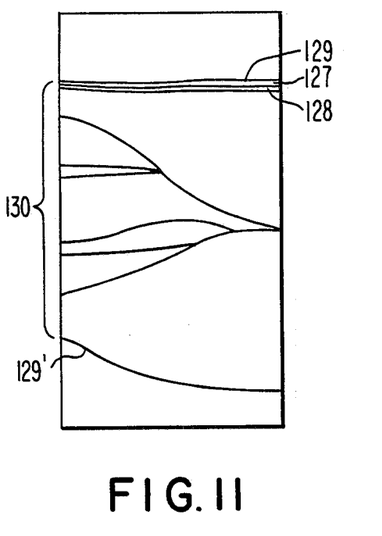
FIG. 11 is a diagrammatic illustration of an ultrasonic transducer image obtained from the ham area of a second hog carcass.
Figure 12:
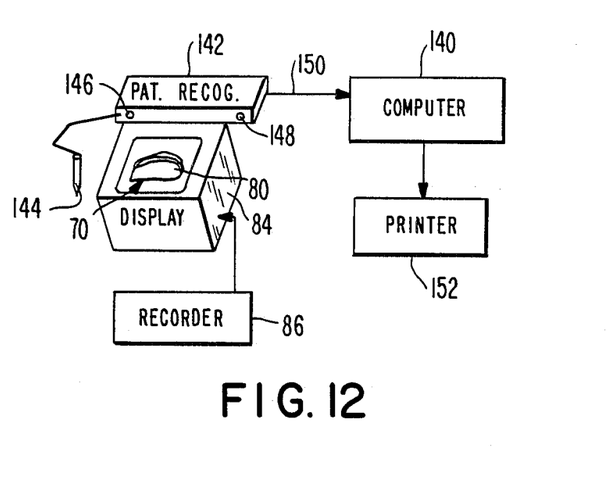
FIG. 12 is a diagrammatic illustration of an alternative embodiment of the system of FIG. 1.

FIGS. 9-11 similarly show the results of ultrasonic imaging of the ham area of a carcass. FIG. 9 illustrates in diagrammatic form the general configuration of a ham 124 cut to show a cross-section, while FIGS. 10 and 11 are diagrammatic representations of ultrasonic images produced from a fatty ham and from a lean ham, respectively, as measured by a ham transducer 20 positioned on the outer surface of the ham. The transducer obtains an image of the ham within the area between the dotted lines 125 and 126. As illustrated, the ham 124 has two layers of fat, indicated at 127 and 128, beneath the skin layer 129, with the meaty area 130 beneath the fatty layers. The layers are joined by connective tissue which shows up well on the ultrasonic image. Note that the ham shown in FIG. 10 has relatively thick layers of fat 127 and 128, while the ham represented by the image in FIG. 11 is relatively lean, with very thin fat layers. The transducer image also shows the skin layer at the opposite side of the ham, as indicated at 129' in FIGS. 10 and 11, to permit determination of the ham thickness and the rate of change of thickness along its length, to thereby permit the grader to determine the meatiness of the ham. Here again, the ultrasonic image provides a clear picture of the relative fat layer thickness and the meatiness of the ham to allow accurate objective grading.

The use of ultrasonic transducers allows hot grading of the carcass; that is, grading immediately after slaughter, rather than requiring that the carcass be chilled for a period of time before grading. This could reduce the energy required in handling the carcass, by eliminating the portion of the energy which is required to cool and then later reheat fat which is to be trimmed away from the carcass after grading prior to chilling. Furthermore, this would avoid the one-day delay involved in the chilling process. Because the transducers are easily positioned and because they give immediate and accurate readings of the areas of interest for grading purposes, and further because images so produced provide a clear picture of the muscling and back fat in a carcass, it is possible with the disclosed apparatus to grade as many as 500-1000 carcasses an hour.

A further improvement in the evaluation of carcasses is provided by the system of the present invention and is illustrated in FIGS. 1 and 8, to which reference is now made. As previously described, the display 84 may be a remote video display unit on which the image produced by the ultrasonic scanner 44 is reproduced. This may be an immediate, or real time, display, as illustrated in the system of FIG. 1, or may be a delayed display produced from a recording of the image, as from the video recorder 86, in the system illustrated in FIG. 8. The display unit 84 may be, for example, a cathode ray display unit which provides an enlarged view of an image such as the image 70.

The grade of a carcass may be evaluated from a visual inspection of the image on display unit 84, or may be evaluated automatically by means of a computer 140 which receives information concerning the image on the unit 84 by way of a suitable pattern recognition device 142 which transfers to the computer information concerning the image. Since one of the factors to be used in evaluating the quality of the carcass is the quantity of meat provided, the pattern recognition device includes a mechanism for scanning the displayed image, such as image 70 from FIG. 6, for example, to determine the area of the meat portion 80, as well as for measuring the thickness of the fat layers 73, 74 and 75.

A suitable pattern recognition device is a GrafBar Model GP-7 Sonic Digitizer, produced by Science Accessories Corporation, 970 Kings Highway West, Southport, Conn., 06490. This Sonic Digitizer 142 includes a stylus 144 and two spaced, point microphones 146 and 148. The digitizer is placed adjacent the flat surface on which the image 70 appears, and the stylus 144 is positioned on the image at a selected location. Pressure on the stylus causes it to emit a high frequency sound which is detected by the microphones 146 and 148, and, by triangulation, the digitizer 142 determines the location, or the coordinates of the location, of the stylus on the image. After determining this first point, which may be used as the origin of the recorded data, the stylus 144 is moved around the periphery of the image to be measured, the operator pressing the stylus on the periphery of the image periodically to produce a series of sonically-generated data points in the digitizer. Alternatively, the stylus can be set to produce a stream of sonic pulses as it is moved around the image. The stylus 144 is used to trace around the entire area 80, for example, returning to the point of origin for the last measurement and thereby providing a series of data points defining the total area of segment 80. These data points may then be transferred to computer 140 by way of cable 150 for storage in the computer and subsequent processing. In addition, the stylus 144 may be used to define the thickness of the fatty layers by producing corresponding data points which are also transferred to the computer. Although there is some subjectivity involved in tracing the outline of the meaty area and of the fatty portions, nevertheless, with some practice in reading ultrasonic images it is relatively easy to trace the desired areas with considerable accuracy, with results that are essentialy reproducible.

The data points stored in the computer are utilized to calculate the meaty area 80 and the thickness of the fatty layers 73, 74, and 75 in the rib eye of the carcass, for both the last rib area and the tenth rib area. For even greater reliability in grading the carcass, similar calculations of the thickness of the fatty areas in the ham, the taper of the ham from one side to the other to provide an indication of its profile, and the meatiness of the ham can also be performed. This information is then used to provide an evaluation of the carcass based upon the selected data, as well as upon the carcass weight, and to provide a printout on printer 152 of the assigned grade for the carcass.

Table 1 provides an illustration of the type of grading available from such a system:

TABLE 1

| Carcass | Hot Carcass Weight (lbs.) | Back Fat (in.) | Muscling (in.) | Grade |
|---|---|---|---|---|
| A | 160 | 1.43 | 5.76 | 3 |
| B | 160 | 1.61 | 5.20 | 4 |

The computer may also calculate the value of each of the carcasses so graded, using the following formula:

Carcass Value = $a + b_1 BF + b_2 C$ Weight $+ b_3 MS$, where a is constant, where $b_1$, $b_2$ and $b_3$ are adjustment factors which are established empirically, BF is the back fat from Table 1, C Weight is the carcass weight from Table 1 and MS is the muscle store, or muscling from Table 1. In a typical example, employing the foregoing formula, carcass A from Table 1 would be valued at $69.98, while carcass B would be valued at $67.06. Thus, the system of the present invention can provide not only an automatic grading of the carcass, but its value as well, and can do so readily and objectively from the two simple measurements produced by the apparatus described above.

A further advantage of the present system of automatic grading is that it is possible to establish a much larger number of grades, since the area and thickness measurement can be made with such high accuracy. Thus, for example, it is contemplated that as many as 100 different grades could be established on the basis of the measurements available by the present system, thus permitting a highly accurate evaluation of each carcass.

Figure 13:
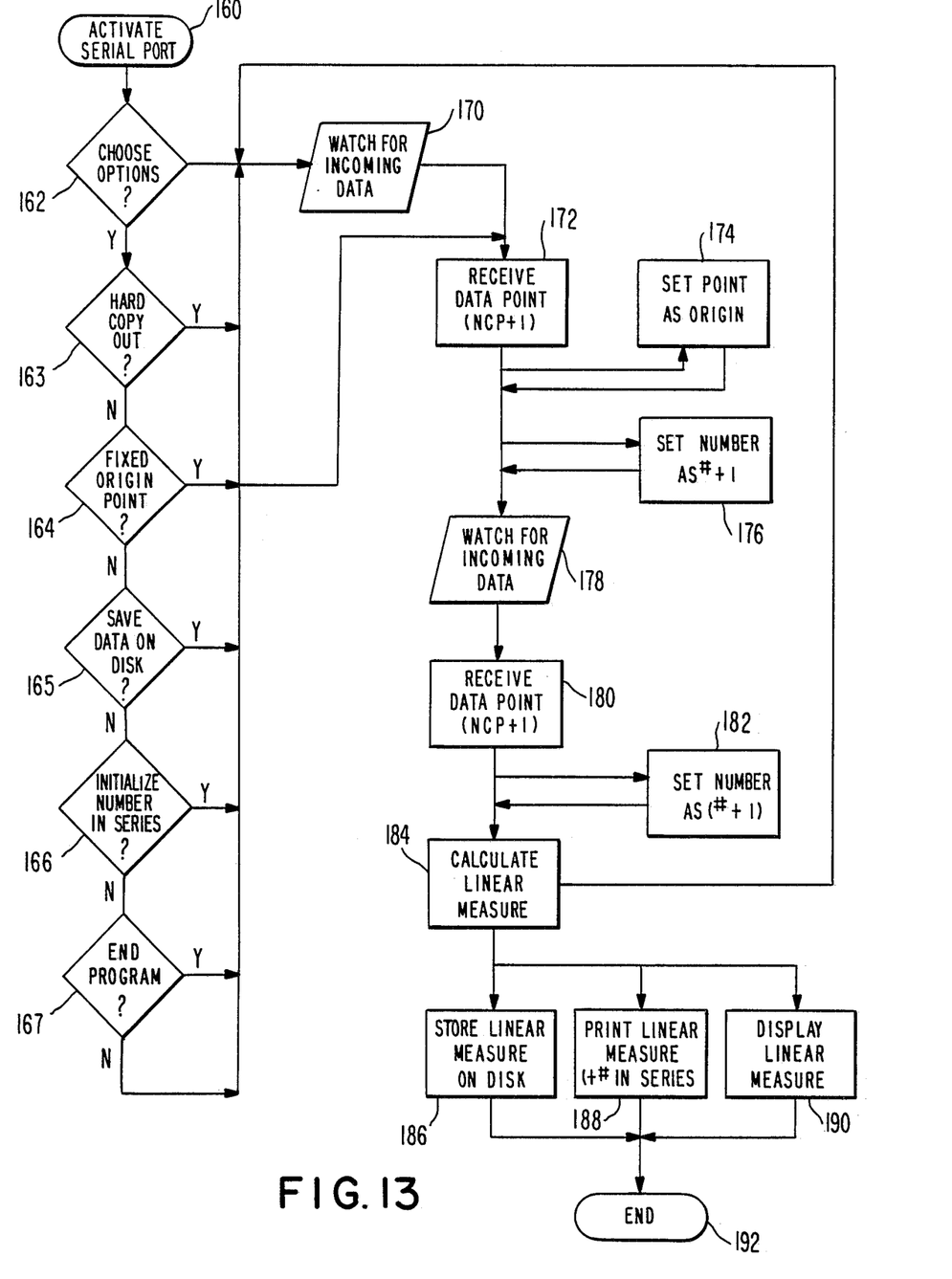
FIG. 13 is a flow diagram of a computer program for the systems of FIGS. 1 and 8.

FIG. 13 is a diagrammatic illustration of a flow chart of a program used in computer 140 for obtaining and storing the linear measurements produced by the Sonic Digizer 142, which is the presently preferred form of the pattern recognition system. Thus, upon activation of the input to the computer, indicated at block 160, and selection of one or more of the various operational options available as indicated in blocks 162–167, the computer is instructed to watch for incoming data from the digitizer, as indicated in block 170. If a fixed origin point is selected, in accordance with selection block 164, that origin point is provided; otherwise, the first data point received according to block 170 is used as the origin. Thus, the first data received at the computer from either the fixed origin point signal or from incoming data from the digitizer is considered as the origin point, and is received by the computer, as indicated at block 172, and is provided as the set point, as indicated at block 174. The incoming data point is assigned an identification number, at signal is then received, as indicated at block 180, the identification number for that data point is increased as indicated at block 182, and the computer then calculates the distance between the two data points, as indicated at block 184. This distance, or linear measure, may be an indication of fat thickness, or it may be the first of a multiplicity of points used to calculate an area. If additional points are to be detected for an area measurement, the computer program loops back to block 170 to receive additional input data points. If not, then the linear measure which has been calculated is stored in memory, as on a disc, as indicated at block 186, is printed on printer 152, as indicated in block 188, or is displayed on a suitable video display, such as the display unit 84, as indicated by block 190, after which the program terminates, as indicated in block 192. A program for carrying out the foregoing detection of data points and calculation of linear distances is contained in Appendix A. A similar program is illustrated in Appendix B, but this program eliminates the provision of a fixed origin point, so that the first data point received acts as the origin.

Calculation of an area enclosed by the linear tracings is carried out in accordance with the program set out in Appendix C. These measurements are then used in the computer 140 to calculate the grade and value of a carcass, as explained above.

Although the present invention has been described in terms of measurements made on a hog carcass, it will be apparent that similar principles may be used in evaluating and grading a beef cattle carcass, although there are some differences in the information received. Specifically, a beef carcass will have only two layers of fat, instead of three, and since the size of the carcass is much greater, much larger transducers must be used or double readings must be taken in order to obtain a full picture of the meat content in the rib area. The use of two overlapping measurements with a small transducer in the rib area of a beef carcass does not present a serious problem in evaluation of the carcass, since each rib eye has a "signature" mark, or discontinuity, in the rib eye pattern which can be used as a reference for the two measurements. This discontinuity allows two separate measurements to be made and then added together to obtain the desired information. Also, since the location of the last rib with respect to the tail is variable in a beef carcass, a fixed transducer mounting arm does not give as accurate a reading as is available with hog carcasses.

It is further noted that the techniques described herein can also be used in evaluting live animals, although the automatic positioning by means of the transducer support arm and collar cannot be used.

Although the present invention has been described in terms of preferred embodiments, it will be apparent to those of skill in the art that numerous variations and modifications may be made without departing from the true spirit and scope thereof, as set forth in the accompanying claims, in which:

What is claimed is:

1. A transducer system for evaluating and grading an animal, comprising:
   a first ultrasonic transducer probe;
   a first transducer support unit for positioning said first ultrasonic transducer probe over a predetermined location along the backbone of the animal for untrasonically scanning a first predetermined region and producing first output signals for measuring back fat and meat quality and quantity in said first region, said first support unit including
   (a) an elongated support arm;
   (b) means at a first end of said support arm for engaging the tail region of the animal and for positioning the support unit along the backbone of the animal; and
   (c) bracket means at a second end of said support arm receiving and securing said first probe, said support arm being adjustable in length to position said probe means over said predetermined location along the backbone of the animal said bracket means securing said first ultrasonic transducer probe so as to direct ultrasonic signals into said first region;
   a second ultrasonic transducer probe;
   a second transducer support unit for positioning said second ultrasonic transducer probe over the upper leg portion of the animal for ultrasonically scanning a second predetermined region for measuring fat thickness and meat quantity and profile, comprising
   (a) collar means shaped to surround and engage the leg portion of the animal; and
   (b) a depending clamp secured to said collar means and receiving and securing said second ultrasonic transducer probe, said collar means being sized and shaped to position said second transducer along the upper leg area of the animal so as to direct ultrasonic signals into said second region;
   means connected to said first and second ultrasonic transducer probes and responsive to said first and second output signals for producing images of the ultrasonically scanned regions of the animal at said predetermined location along the backbone and along said upper leg area, said images permitting visual grading of the aniaml.

2. The transducer system of claim 1, further including means responsive to said first output signals from said first ultrasonic transducer probe for providing data relative to fat thickness in said ultrasonically scanned region along the backbone of the animal.

3. The transducer system of claim 1, further including means responsive to said second output signals from said second ultrasonic transducer probe for providing data relating to meat area and profile in said ultrasonically scanned region along said upper leg area of the animal.

4. The transducer system of claim 1, further including means responsive to said first and second output signals from said first and second ultrasonic transducer probes for providing data relating to fat thickness, meat area, and meat profile in said ultrasonically scanned regions of the animal.

5. The transducer system of claim 4, further including means responsive to said data to determine a grade to be assigned to said animal.

6. The transducer system of claim 4, wherein said means responsive to said first and second ultrasonic transducer probes output signals includes digitizer means producing output signals corresponding to the relative locations of fat and meat areas in said ultrasonically scanned regions; and
   means responsive to said digitizer output signals for calculating the meat area and fat thickness in said regions to thereby determine a grade to be assigned to the animal.

7. The transducer system of claim 6, wherein said digitizer means is a sonic digitizer.

8. The transducer system of claim 1, further including a third ultrasonic transducer probe, and wherein said first support unit further includes second bracket means spaced from said first-named bracket means at the second end of said support arm, said second bracket means receiving and securing said third ultrasonic transducer probe to locate it over a second predetermined location along the backbone of the animal for ultrasonically scanning a third predetermined region for measuring back fat and meat quality and quantity in said third region to obtain ultrasonic images of back fat and meatiness at two spaced regions along the backbone.

9. The transducer system of claim 8, wherein said support arm is sufficiently long and said first and second bracket means are so located as automatically to position said first-named ultrasonic probe over the last rib area of an animal and said third ultrasonic probe over the tenth rib area of the animal when said means at said first end of said support arm engages the tail region of the animal.

10. A method for evaluating an animal, comprising:
    positioning ultrasonic transducer means over a preselected rib area of an animal to be graded;
    driving said transducer means by an ultrasonic scanner to obtain an ultrasonic cross-sectional image of the back fat layers and rib eye meat within said preselected rib area of the animal;
    displaying said ultrasonic image;
    measuring on said image the fat thickness dimensions and storing the measured dimensions;
    measuring on said image the periphery of the meat portion of said image;

calculating from the measurements of periphery the area of said meat portion and storing the meat area calculation; and obtaining from said back fat thickness measurements and meat area calculation, a grade evaluation for the animal.

11. The method of claim 10, further including positioning ultrasonic transducer means over a second preselected rib area of an animal to be graded;

driving said transducer means by an ultrasonic scanner to obtain a second ultrasconic cross-sectional image of the back fat layers and rib eye meat within said second preselected rib area of the animal;

displaying said second ultrasonic image;

measuring on said second image the fat thickness dimensions and storing the measured dimensions;

measuring on said second image the periphery of the meat portion of said second image;

calculating from the measurements of periphery on said second image the area of said second image meat portion and storing the meat area calculation; and obtaining, from said stored first and second image measurements of the thickness of said back fat layers and from said stored first and second calculations of the area of said rib eye meat in said first and second preselected rib areas of he animal, a grade evaluation for the animal.

12. The method of claim 11, further including positioning ultrasonic transducer means on a third preselected portion of an animal to be graded;

driving said transducer means by an ultrasonic scanner to obtain a third ultrasonic cross-sectional image of the fat layers and meatiness of said third preselected portion of the animal;

displaying said third ultrasonic image;

measuring on said third image the fat thickness dimensions and storing the measured third image dimensions;

measuring on said third image the profile of the meat portion of said third image and storing measured third image profile data;

measuring on said third image the periphery of the meat portion of said third image;

calculating, from the measurement of said third image periphery, the area of the meat portion of said third preselected portion and storing the meat area calculation; and obtaining, from said stored first, second and third image measurements and calculations a grade evaluation for the animal.

13. A transducer system incorporating a positioning device for locating at least one transducer adjacent a predetermined region of an animal to be evaluated, the system comprising:

at least one ultrasonic transducer probe;

a transducer support unit having an elongated arm, engagement means to a first end of said arm for engaging a predetermined first region of an animal to be evaluated and for positioning said elongated arm along the backbone of the animal; and bracket means mounted at a second end of said arm for receiving and securing said at least one transducer probe so as to direct ultrasonic signals from said probe into a preselected, fixed second region of the animal adjacent its backbone to obtain an ultrasonic image of the back fat and meat quality and quantity in said second region;

display means electrically connected to said at least one transducer probe and responsive to said probe for displaying a cross-sectional image of said second region for real-time evaluation of the animal;

pattern recognition means responsive to said cross-sectional image for providing measurements of the thickness of the back fat and the area and quality of the meat in said second region; and means responsive to said pattern recognition means measurements for providing detailed analysis and evaluation of the animal.

14. The system of claim 13, wherein said pattern recognition means comprises:

means for tracing said cross-sectional image of said second region to obtain data points defining the perimeter of the meaty portion and the edges of the fatty portions of said second region; and means responsive to said data points for calculating the area of said meaty portion and the thickness of said fatty portions for said second region.

15. The system of claim 14, wherein said means responsive to said pattern recognition means measurements comprises means responsive to said area and thickness calculations for assigning a grade and value to the animal.

16. The transducer system of claim 13, wherein said engagement means includes a hook for engaging the tail region of an animal carcass to be evaluated, and wherein said bracket means positions said at least one transducer probe adjacent the region of the last rib of the animal carcass.

17. The transducer system of claim 6, wherein said bracket means includes first and second spaced brackets, each receiving a corresponding one of first and second transducer probes, said first bracket positioning said first transducer probe adjacent said fixed second region, and said second bracket positioning said second transducer probe adjacent a fixed third region, and wherein said display means is selectively connected to said first or said second transducer probe for displaying a cross-sectional image of said second region or of said third region, respectively, for real-time evaluation of the animal carcass.

18. The transducer system of claim 17, wherein said pattern recognition means comprises:

means for tracing a cross-sectional image of said first or second regions to obtain data points defining the perimeter of the meaty portion and the edges of the fatty portions of the respective region images; and means responsive to said data points for calculating the areas of said meaty portions and the thicknesses of said fatty portions for each of said second and third regions.

19. The transducer system of claim 18, wherein said means responsive to said pattern recognition means measurements comprises means responsive to said area and thickness calculations for said second and third regions for assigning a grade and value to the animal carcass.

20. A method for evaluating an animal by measurement of the fat content and meatiness of one or more preselected regions of the animal, comprising positioning an ultrasonic transducer over a selected area in the region of the backbone of the animal to be evaluated;

driving the transducer to produce ultrasonic signals which scan said selected area to produce an ultrasonic cross-sectional image of the fat layers and meatiness of said selected area;

displaying said image;

measuring on said image the fat thickness dimensions, and storing the measured dimensions in a computer;

measuring on said image the periphery of the meat portion of said image;

calculating from said measurements of periphery the area of said meat portion and storing said calculated area in the computer; and determining from said stored measured dimensions and said stored calculated area a grade evaluation for the animal.

21. The method of claim 20, wherein the step of measuring the periphery of the meat portion of said image comprises tracing the meat areas on said displayed image by means of a stylus;

while tracing the meat areas, periodically determining the coordinates of the stylus on said image to obtain a series of area data points representing the boundary of said meat area; and transferring said data points to the computer for use in calculating the area circumscribed by said data points to thereby determeine the area of said meat portion.

22. The method of claim 21, wherein the step of measuring said fat thickness dimensions comprises:

tracing the fat portions on said displayed image by means of a stylus;

while tracing the fat portions, periodically determining the coordinates of the stylus on said image to obtain a series of thickness data points representing the boundaries of said fat portions; and transferring said data points to the computer for use in determining the thickness of the fat portions.

* * * * *

UNITED STATES PATENT AND TRADEMARK OFFICE
CERTIFICATE OF CORRECTION

PATENT NO. : 4,785,817
DATED : November 22, 1988
INVENTOR(S) : Stouffer

It is certified that error appears in the above-identified patent and that said Letters Patent is hereby corrected as shown below:

Claim 1, line 3, column 12, "aniaml" should be --animal--.

Claim 2, line 7, column 12, "relative" should be --relating--.

Claim 11, line 27, column 13, "he" should be --the--.

Claim 12, line 58, column 13, "to" should be --at--.

Claim 17, line 33, column 14, "6" should be --16--.

Signed and Sealed this

Ninth Day of May, 1989

Attest:

DONALD J. QUIGG

Attesting Officer

Commissioner of Patents and Trademarks